(12) United States Patent
Huang

(10) Patent No.: US 10,603,406 B2
(45) Date of Patent: Mar. 31, 2020

(54) HYDROGEL FOR CELL CULTURE AND BIOMEDICAL APPLICATIONS

(71) Applicant: TheWell Bioscience, Newark, NJ (US)

(72) Inventor: Hongzhou Huang, Newark, NJ (US)

(73) Assignee: THEWELL BIOSCIENCE, Newark, NJ (US)

( * ) Notice: Subject to any disclaimer, the term of this patent is extended or adjusted under 35 U.S.C. 154(b) by 0 days.

(21) Appl. No.: 15/949,457

(22) Filed: Apr. 10, 2018

(65) Prior Publication Data

US 2018/0289856 A1    Oct. 11, 2018

Related U.S. Application Data

(60) Provisional application No. 62/483,831, filed on Apr. 10, 2017.

(51) Int. Cl.

| | |
|---|---|
| *A61L 27/20* | (2006.01) |
| *A61L 27/26* | (2006.01) |
| *A61L 27/38* | (2006.01) |
| *A61L 27/52* | (2006.01) |
| *A61L 27/54* | (2006.01) |
| *C12N 5/071* | (2010.01) |
| *C08L 5/00* | (2006.01) |
| *C08B 37/00* | (2006.01) |
| *C12N 5/00* | (2006.01) |

(52) U.S. Cl.
CPC ............... *A61L 27/20* (2013.01); *A61L 27/26* (2013.01); *A61L 27/3895* (2013.01); *A61L 27/52* (2013.01); *C08B 37/006* (2013.01); *C08L 5/00* (2013.01); *C12N 5/0068* (2013.01); *C12N 5/0677* (2013.01); *A61L 27/54* (2013.01); *A61L 2400/06* (2013.01); *A61L 2430/34* (2013.01); *C08L 2203/02* (2013.01); *C08L 2205/025* (2013.01); *C08L 2205/03* (2013.01); *C08L 2205/035* (2013.01); *C12N 2513/00* (2013.01); *C12N 2533/70* (2013.01)

(58) Field of Classification Search
CPC .......... A61L 27/20; A61L 27/26; A61L 27/38; A61L 27/52; A61L 27/54; C12N 5/071; C08L 5/00

See application file for complete search history.

(56) References Cited

U.S. PATENT DOCUMENTS

| | | | |
|---|---|---|---|
| 2,348,448 | A | 5/1944 | Brewer |
| 5,468,638 | A | 11/1995 | Barker et al. |
| 7,598,076 | B2 | 10/2009 | Wedell et al. |
| 9,579,417 | B2 | 2/2017 | Pereira Da Silva et al. |
| 2003/0186217 | A1 | 10/2003 | Bader |
| 2008/0220526 | A1 | 9/2008 | Ellison et al. |
| 2013/0267019 | A1 | 10/2013 | Schmidt et al. |
| 2014/0322806 | A1 | 10/2014 | Bennett et al. |

FOREIGN PATENT DOCUMENTS

| | | |
|---|---|---|
| CN | 106474560 | 3/2017 |
| EP | 0590485 A1 | 4/1994 |
| EP | 0590485 B1 | 4/1994 |
| EP | 0590513 | 4/1994 |
| EP | 1053790 | 11/2000 |
| RU | 2597978 | 9/2016 |
| WO | 2010/143196 | 12/2010 |
| WO | 2014017513 | 1/2014 |
| WO | 2014025312 | 2/2014 |

OTHER PUBLICATIONS

International Search Report dated Aug. 2, 2018 in corresponding PCT Application No. PCT/US2018/026854.
Pereira D.R. et. al., Development of a Gellan Gum-Based Microparticlesl Hydrogel Matrices for Application in the Intervertebral Disc Regeneration. Tissue Engineering, Part C, 2011, vol. 17, No. 10, pp. 961-972.

*Primary Examiner* — Zohreh A Fay
(74) *Attorney, Agent, or Firm* — Gearhart Law LLC

(57) ABSTRACT

Described herein are preparations and applications of gellan gum hydrogel for cell culture and biomedical applications, including 2D coating culture, 3D cell culture, and injection. The gellan gum materials for such application include water soluble low acyl gellan gum, high acyl gellan gum, modified gellan gum and a mixture of gellan gum mixture with other chemical/biological molecules.

40 Claims, 5 Drawing Sheets

HYDROGEL FOR CELL CULTURE AND BIOMEDICAL APPLICATIONS

CLAIM OF PRIORITY

This application claims priority to U.S. Application 62/483,831 filed on Apr. 10, 2017, the contents of which are herein fully incorporated by reference in its entirety.

FIELD OF THE EMBODIMENTS

The field of the embodiments of the present invention relate to the use of hydrogels for cell culture and various other biomedical applications. More specifically, the embodiments of the present invention relate to the preparation and application of gellan gum hydrogel for cell culture and biomedical applications, including but not limited to, 2D coating culture, 3D cell culture, and injection.

BACKGROUND OF THE EMBODIMENTS

People are increasingly aware of the lack of ability of 2D cell culture to predict the complex behavior of a biological system of many different interacting cell types and to reproduce the anatomy or physiology of a tissue for informative or useful study. 3D cell culture models are a more accurate representation of the natural environment experienced by the cells in the living organism, which allows for intercellular interactions with more realistic biochemical and physiological responses. In 3D cell cultures, cells behave and respond more like they would in vivo to internal and external stimuli, such as changes in temperature, pH, nutrient absorption, transport, and differentiation. Therefore, scientists are shifting their focus from 2D to 3D cell cultures in the fields of drug screening, tissue engineering, preclinical study, cell therapy, and basic cell biological study.

To mimic in vivo cell growing conditions, the reticulated structure of 3D scaffold should be serialized, have a high water content, and have a number of other desirable characteristics such as accurate 3D spatial support, suitable mechanical strength, and facile transportation of oxygen, nutrients, waste, and soluble factors. Mild and cytocompatible conditions for sol-gel transformation are preferred, to ensure that cells survive comfortably during both cell encapsulation and isolation. Moreover, the injectable property of biomaterial used for 3D cell culture is critical for downstream applications such as cancer therapy (xerography study for drug discovery), tissue regeneration, and 3D bio-printing.

The current materials for 3D cell cultures on the market can be classified as hydrogels, polymer matrices, hanging drop plates, low adhesion plates, micro-patterned surfaces, and magnetic levitations. Hydrogel scaffolds have been demonstrated as the most promising approach to date in facilitating 3D cell culture. However, most existing biomaterials (including hydrogel scaffolds) for 3D cell cultures are limited to physiological conditions (e.g. poor scaffold structure, unwanted growth factors, and undesirable pH or temperature of pre-gel solution), complex operating steps for cell encapsulation, difficulties for cell isolation from culture scaffold, and product reproducibility. In addition, injectable properties, such as shear-thinning and rapid recovery of physical strength, in currently marketed hydrogel materials is very rare. This drawback not only affects the data generated from these 3D cell culture technologies but also limits the applications of this technology for downstream analysis and clinical applications. Examples of related art are described below:

U.S. Patent Application No. 2008/0220526 pertains to coatings for cell culture surfaces. More particularly, this invention relates to coatings for cell culture surfaces which are derived from or contain gums including naturally occurring gums, plant gums, galactomannan gums or derivatives thereof. The invention also relates to articles of manufacture (e.g., cell culture vessels and labware) having such coatings, methods of applying these coatings to cell culture surfaces, and methods of using coated cell culture vessel.

U.S. Pat. No. 9,579,417 pertains to cell-adhesive gellan gum spongy-like hydrogels that are able to entrap/encapsulate adherent cells, which spread within the material, maintaining their phenotype and remaining viable and proliferative. The methodology used to obtain these materials involves hydrogel preparation, freezing, freeze-drying and re-hydration with a saline solution with cells and with/without bioactive molecules. No pre and/or post functionalization of the spongy-like hydrogels with cell adhesive features, as used for other hydrogels, is used. The cell adhesive character of these materials, not observed in hydrogels, is in part explained by their physical properties, between sponges and hydrogels, dissimilar from the precursor hydrogels. The physical properties that are mainly different are the morphology, microstructure, water content, and mechanical performance. Gellan gum spongy-like hydrogels physical properties and biological performance can be tuned by manipulating the parameters involved in spongy-like hydrogel formation. Bioactive molecules can also be entrapped with or without cells to modify the biological performance of the spongy-like hydrogels. These materials can be applied in the context of bioengineering, tissue engineering, regenerative medicine and biomedical applications.

Chinese Patent Application No. 106474560 pertains to the technical field of biological material, discloses for 3D biological printing of the hydrogel material and its preparation method and application. Hydrogel material of this invention comprises the following mass percentage component: and/or its derivatives to form the 0.5-10%, PEG and/or its derivatives 0.1-20%, cross-linking initiator 0-1%, biological active component 0-15%, the rest of the solvent. The invention is based on the form the hydrogel material and PEG double-network hydrogel, physiological environment forming an interpenetrating double-network structure, has better structure and size stability, has fast gel under physiological conditions, cell with good biocompatibility, immune rejection small, cell encapsulation rate high, the mechanical strength of the controllable, biodegradable and the like. And applied to the 3D in biological printing, overcomes the slow curing speed, curing conditions are harsh, mechanical property is limited, cells poor compatibility, has obvious advantages and good industrialization prospects.

PCT Patent Application No. WO2014025312 pertains to a method of manufacturing hydrogel microparticles comprising one or more species of living cells attached thereon and/or encapsulated therein is provided. The method includes dissolving a hydrogel-forming agent in an aqueous medium to form a solution; suspending one or more species of living cells in the solution to form a cell suspension; dispersing the cell suspension into an organic oil to form a microemulsion; and subjecting the microemulsion to conditions that allow the hydrogel-forming agent to form hydrogel microparticles comprising one or more species of living cells attached thereon and/or encapsulated therein. Composition comprising a mixture of a degradable hydrogel and at least one hydrogel microparticle having one or more species of living cells, and method of manufacturing a scaffold for tissue engineering are also provided.

PCT Patent Application No. 2014017513 pertains to a method for culturing a cell and/or a tissue, said method being characterized by culturing the cell and/or the tissue in a floated state using a culture medium composition, wherein amorphous structures are formed in a liquid culture medium, are dispersed in the solution uniformly, and substantially hold the cell and/or the tissue without substantially increasing the viscosity of the solution, so that the culture medium composition has an effect of preventing the sedimentation of the structures; and others.

None of the art described above addresses all of the issues addressed by the embodiments of the present invention. There clearly exists an unmet need for finding compositions and methods for preparing gellan gum hydrogel systems that are suitable for cell culture and various biomedical applications, including but not limited to, 2D coating culture, 3D cell culture, and injection.

SUMMARY OF THE EMBODIMENTS

In one of the embodiments of the present invention, there is a composition for preparing a polysaccharide hydrogel having one or more water soluble high acyl gellan gum polymers; one or more water soluble low acyl gellan gum polymers; and one or more water soluble chemically modified gellan gum polymers.

In at least one embodiment, sodium citrate is added to the gellan gum polymer solution and the pH of the gellan gum polymer solution is adjusted to a neutral pH (approximately pH of 6-8).

In at least one embodiment, dry powder of the gellan gum is prepared by: 1) addition of 2-propanol and drying overnight; or 2) freeze-drying.

In at least one embodiment, the gellan gum is dissolved in water or an aqueous solution at room temperature.

In another embodiment of the present invention, there is provided a composition for preparing a polysaccharide hydrogel, wherein the polysaccharide hydrogel formed is a soft gel suitable for injection uses, to which a bioactive molecule can further be added, encapsulated within the hydrogel and delivered to a different location for use.

In one embodiment, there is provided a composition for preparing a polysaccharide hydrogel, wherein the soft gel exhibits shear thinning and self-healing rheological properties, by allowing the polysaccharide hydrogel to be converted into a liquid state by a shearing force, or to recover its hydrogel state once the shearing force is ceased and further the gel-sol states can be transformed multiple times.

In another embodiment, there is provided a composition for preparing a polysaccharide hydrogel, wherein the shearing force is exerted by pipetting, syringe injection or pump perfusion.

In yet another embodiment of the present invention, there is provided a composition for preparing a polysaccharide hydrogel, wherein the polysaccharide hydrogel formed is a hard gel, to which bioactive molecules can further be added and encapsulated within the hydrogel.

In one embodiment, there is provided a composition for preparing a polysaccharide hydrogel, wherein the hard gel exhibits 3-D gel structures with rheological properties such that when the hard gel is broken by pipetting or injection (shearing), it breaks into small gel particles, and it has an affinity for, and can be modified by, a bioactive molecule.

In another aspect of the embodiment, it is provided a composition for preparing a polysaccharide hydrogel, wherein the hydrogel has a storage modulus value of greater than about 10 Pa.

In another embodiment, there is provided a composition for preparing a polysaccharide hydrogel, wherein the hard hydrogel can maintain its gel formation intact at a temperature equal to or below about 80° C., but can be broke into small gel particles when disturbed with external force.

In yet another embodiment of the present invention, there is provided a composition for preparing a polysaccharide hydrogel, wherein the one or more chemical molecules are selected from the group consisting of: a) organic molecules that are selected from the group consisting of: polymers of natural or synthetic origin, chemically modified or copolymers, polypeptide, hyaluronate, chitosan, collagen, polyethyleneglycol anticoagulants, contrasting agents, chemotherapeutic agents, and signaling pathway molecules; and b) inorganic molecules that are selected from the group consisting of: bioactive glass, hydroxyapatite, calcium phosphate and iron.

In yet another embodiment of the present invention, there is provided a composition for preparing a polysaccharide hydrogel, wherein the one or more bioactive molecules that can be added into the gellan gum solution are selected from the group consisting of: cells, peptides, proteins, lipids, polysaccharides, growth factors, growth hormone, antibodies, enzymes, cell receptors, cell ligands, antibiotics, antimicrobial, anti-fungi, antimycotics, functional peptide molecules with $NH_2$, COOH and $CONH_2$ group comprising: RGD, IKVAV, REDV, YIGSRY, poly Lysine.

In still another embodiment of the present invention, there is provided a method for preparing a bioactive-molecular-modified (such as peptide-modified) gellan gum solution by adding a peptide into the gellan gum solution as a mixture and then heating at a temperature of about 100° C. or above and a pressure of about 1 to about 40 psi, more preferably about 1 to about 30 psi, and for a time period of about 3 to about 30 min, more preferably for about 5 to about 20 min. Such bioactive-molecular-modified gellan gum solution can be used for forming a polysaccharide hydrogel by being mixed with cell culture medium.

In still another embodiment of the present invention, there is provided a composition for preparing a polysaccharide hydrogel, wherein the soft gel is converted into a hard gel by being submerged in or added with an aqueous solution of extra phosphate buffer, cell culture media or ionic solutions, or a combination thereof.

In yet another embodiment of the present invention, there is provided a composition for preparing a polysaccharide hydrogel, wherein the one or more bioactive molecules are in contact with, adhered to, suspended, embedded or entrapped in the polysaccharide hydrogel system while maintaining their bioactivities.

In another embodiment of the present invention, there is provided a composition for preparing a polysaccharide hydrogel, wherein the one or more bioactive molecules are suspended or entrapped in the polysaccharide hydrogel while maintaining their bioactivities.

In another embodiment of the present invention, there is provided a composition for preparing a hard polysaccharide hydrogel, wherein the one or more bioactive molecules are in contact with, adhered to, suspended, embedded or entrapped in the polysaccharide hydrogel system while maintaining their bioactivities.

In yet another embodiment of the present invention, there is provided a composition for preparing a hard polysaccharide hydrogel, wherein the one or more bioactive molecules are suspended or entrapped in the polysaccharide hydrogel while maintaining their bioactivities.

In yet another embodiment of the present invention, it is provided a composition for preparing a polysaccharide hydrogel, wherein the one or more low acyl gellan gum polymers have a range of the degree of acylation from about 1 to 4 glycerate(s) per repeat and 1 to 4 acetate(s) per every two repeats.

In yet another embodiment of the present invention, there is provided a composition for preparing a polysaccharide hydrogel, wherein the composition comprises from about 0.001% to about 20% of the one or more high acyl gellan gum polymers, about 0.001% to about 20% of the one or more low acyl gellan gum polymers, about 0.001% to about 20% of the one or more modified gellan gum polymers, and further comprises from about 0.00001% to about 30% of the one or more bioactive molecules.

In one embodiment of the present invention, there is provided a composition for preparing a polysaccharide hydrogel, wherein the composition has a storage modulus value of greater than about 10 Pa.

In another embodiment of the present invention, the hard hydrogel system can maintain its gel formation at temperature equal to or below about 100° C.

In yet another embodiment of the present invention, there is provided a composition for preparing a polysaccharide hydrogel, wherein the composition comprises from about 0.01% to about 5% of the one or more high acyl gellan gum polymers, about 0.01% to about 5% of the one or more low acyl gellan gum polymers, about 0.01% to about 5% of the one or more modified gellan gum polymers, and further comprises from about 0.001% to about 10% of the one or more bioactive molecules.

In one embodiment of the present invention, there is provided a composition for preparing a polysaccharide hydrogel, wherein the composition has a storage modulus value of 10 to 20000 Pa.

In another embodiment of the present invention, wherein the hard hydrogel system can maintain its hydrogel formation at temperature equal to or below about 80° C.

In yet another embodiment of the present invention, there is provided a method for forming a polysaccharide hydrogel comprising the steps of: dissolving the water-soluble gellan gum polymers in a water based solvent with solid content higher than 0.001% w/v at a temperature ranging from about 4° C. to about 80° C.; heating the solution to a temperature of about 100° C. or higher and at a pressure of about 1-10 psi or higher for 3 min or longer; reticulation at a temperature ranging from about 4° C. to about 50° C. by directly mixing the solution with phosphate buffer (PBS), cell culture media or ionic solutions to trigger entire mixture to be transformed into a hydrogel system, wherein the system's storage modulus (G') increases upon mixing and surpasses 10 Pa within 30 min, such that the system can sustain bioactive molecules suspended within its hydrogel matrix for 3D growth; and adding chemicals or bioactive molecules such that they can be in contact with, adhered to, suspended, embedded or entrapped in the polysaccharide hydrogel formed.

In one embodiment of the present invention, there is provided a method for forming a polysaccharide hydrogel, wherein the water based solvent comprises water, phosphate buffer solution (PBS), saline solution, cell culture medium, ionic solution, albumin, serum and xyloglucan.

In another embodiment of the present invention, there is provided a method for forming a polysaccharide hydrogel, wherein the solid content is used in amounts ranging from about 0.001% (w/v) to 50% (w/v).

In yet another embodiment of the present invention, there is provided a composition for preparing a soft polysaccharide hydrogel, wherein the soft gel system formed is converted into a hard gel system by adding the additional trigger solution of an ionic concentration of 10 mg/L or higher to soft hydrogel system In yet another embodiment of the present invention, there is provided a composition for preparing a soft polysaccharide hydrogel, wherein the soft gel formed is converted into a hard gel system by being submerged in an aqueous solution of cell culture media or ionic solution.

In one embodiment of the present invention, there is provided a composition for preparing a soft polysaccharide hydrogel, which is converted to a hard hydrogel by using the aforementioned conversion method, wherein the bioactive molecules can be added into the hydrogel system before or after the hydrogel formation, or before or after the exchange of hydrogel and the surrounding media, by being mixed with the gellan gum solution or trigger solutions.

In yet another embodiment of the present invention, there is provided a use of a polysaccharide hydrogel derived from an aforementioned composition as a versatile platform for drug discovery and biomedical applications, comprising cell viability assay, live/dead assay, high-throughput screening, fluorescent staining and imaging, histological analysis, and 3D bio-printing.

In one embodiment of the present invention, there is provided a use of a polysaccharide hydrogel derived from an aforementioned composition, wherein living cells are grown on the top of, or embedded, encapsulated in the hydrogel and are harvested out of hydrogel system by breaking the hydrogel and dissolving the hydrogel with DI water or low ionic concentration solution.

In another embodiment of the present invention, there is provided a use of a polysaccharide hydrogel derived from an aforementioned composition, wherein a convenient two-step procedure is provided for in vitro 3D cell culture in the hydrogel, comprising: 1) Living cells can be mixed with polysaccharide solution or trigger solution such as cell culture media before the hydrogel formation. The cells are homogeneously suspended in the soft hydrogel and ready to transfer to an individual cell culture plate or different container by pipetting or injection; and 2) Once the soft gel (with cells) is placed in the final container, the extra trigger solutions can be added on the top or surround the soft gel and convert it into the hard hydrogel; wherein the 3D matrix structure is further stabilized and nutrition or other biomolecules can be added into the hydrogel system and exchange between the hydrogel and surrounding media.

In yet another embodiment of the present invention, there is provided a use of a polysaccharide hydrogel derived from an aforementioned composition for 2D hydrogel coating cell culture, wherein the soft hydrogel is added directly to the surface of the culture plate to coat the cell culture plate, and then living cells can be added on the top of hydrogel and grow in 2D and some cells can penetrate into hydrogel from the top and grow as 3D structure.

It is an object for the present invention to provide compositions and methods for preparing gellan gum hydrogel systems that are suitable for cell culture and various biomedical applications, including but not limited to, 2D coating culture, 3D cell culture, and injection. The gellan gum materials for such application include water soluble low acyl gellan gum, high acyl gellan gum, modified gellan gum and a mixture of gellan gum mixture with other chemical/ biological molecules. Biomolecules can be added into the hydrogel system before or after hydrogel formation and exchange of hydrogel and the surrounding media. Cells can be added into the hydrogel system before or during the hydrogel formation by mixing with gellan gum solution or trigger solutions. The cell can growth on the top of hydrogel or encapsulated to grow for a 3D structure such as cell colony. Cells can be harvested out of hydrogel by breaking the hydrogel and dissolve the hydrogel with DI water or low ionic concentration solution. Such a hydrogel system provides a versatile platform for drug discovery, 3D bioprinting, high-throughput screen and medical devices.

DESCRIPTION OF THE PREFERRED EMBODIMENTS

Figure 1:
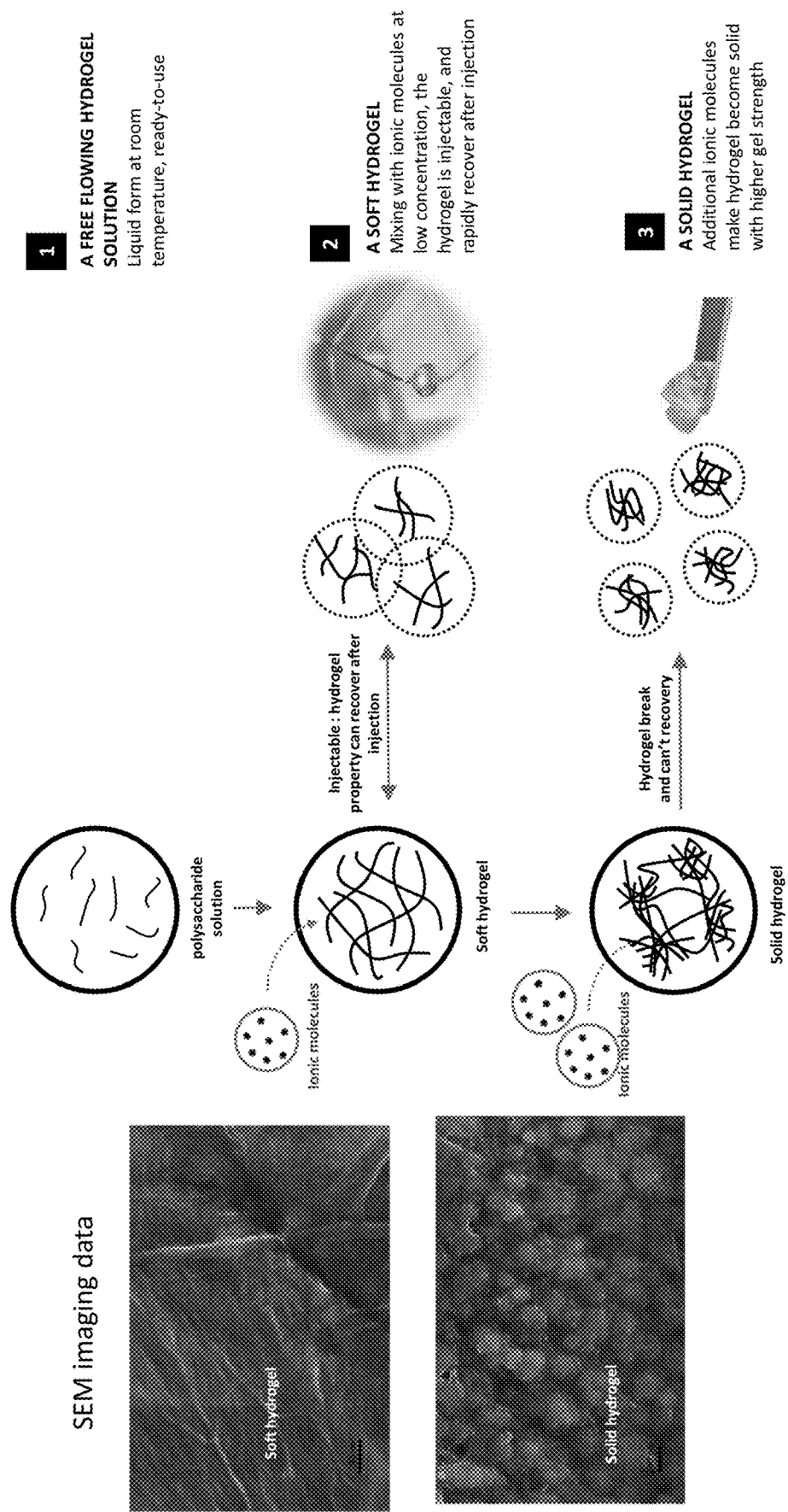
FIG. 1 is a diagram detailing properties of the soft and hard hydrogels of embodiments of the present invention.

Gellan gum is a water-soluble anionic capsular polysaccharide produced by the bacterium *Sphingomonas elodea* (formerly *Pseudomonas elodea*). The gellan-producing bacterium was discovered and isolated by the former Kelco Division of Merck & Company, Inc. in 1978 from the lily plant tissue from a natural pond in Pennsylvania, USA. It was initially identified as a substitute gelling agent at significantly lower use level to replace agar in solid culture media for the growth of various microorganisms. (Kang K. S., et al., Agar-like polysaccharide produced by a *Pseudomonas* species: Production and basic properties. Applied & Environmental Microbiology, 1982 43: 1086-1091). The initial gellan gum commercial product with the trademark as "GELRITE" was subsequently identified as a suitable agar substitute as gelling agent in various clinical bacteriological media. (Shungu D, et al., GELRITE as an Agar Substitute in Bacteriological Media, Appl. Environ Microbiol. 1983 46(4): 840-5) As a food additive, gellan gum was first approved for food use in Japan (1988). Subsequently, gellan gum has been approved for food, non-food, cosmetic and pharmaceutical uses by many other countries such as U.S., Canada, China, Korea, European Union, etc. It is widely used as a thickener, emulsifier, and stabilizer.

Gellan gum is manufactured by fermenting an appropriate strain of *Sphingomonas* with a readily available carbohydrate source. The constituent sugars of gellan gum are glucose, glucuronic acid and rhamnose in the molar ratio of 2:1:1. These are linked together to give a primary structure comprising a linear tetrasaccharide repeat unit (O'Neill M. A. et al., Carbohydrate Research, Vol. 124, p. 123, 1983; Jansson, P. E. et al., Carbohydrate Research, Vol. 124, p. 135, 1983). In the native or high acyl form of gellan gum, two acyl substituents, acetate and glycerate, are present. Both substituents are located on the same glucose residue and, on average, there is one glycerate per repeat unit and one acetate per every two repeat units. In the low acyl form of gellan gum, the acyl groups have been removed to produce a linear repeat unit substantially lacking such groups. Deacylation of the gum is usually carried out by treating a fermentation broth with alkali.

Shown below in Table 1 are gellan gum (of molecular weights ranging from $5 \times 10^4$ Da to $2 \times 10^6$ Da) with different level of acyl (A-high acyl gellan gum), no/low acyl gellan gum (B) or chemical modified gellan gum such as methacrylated gellan gum (C).

TABLE 1

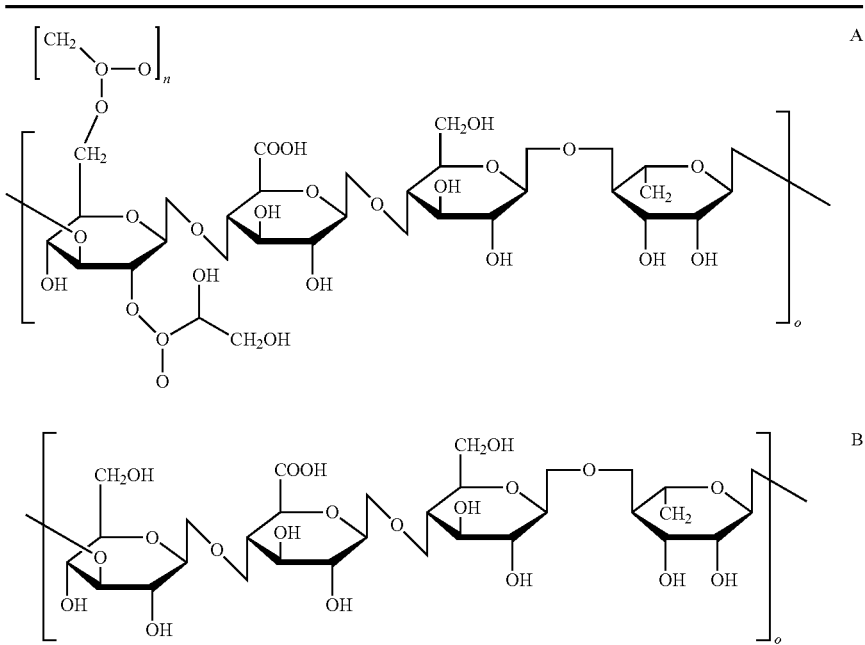

TABLE 1-continued

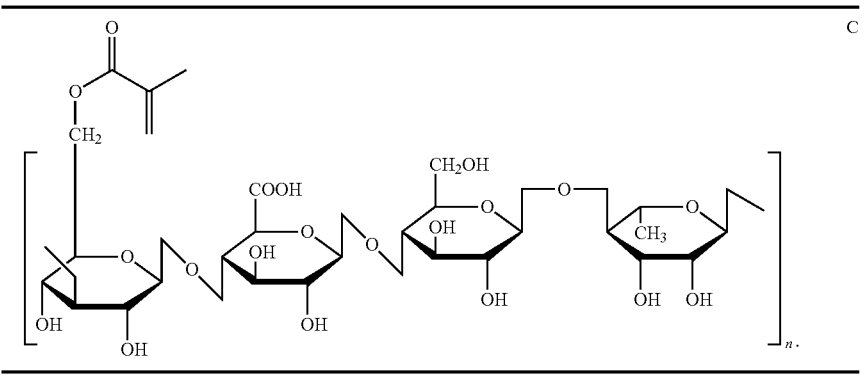

The high acyl form of gellan gum does not require addition of any substances for gel formation provided the gum concentration is higher than the critical concentration. High acyl gellan gum produces a soft, elastic, and non-brittle gel when its solution is cooled below the setting temperature. High acyl gellan gum gels will soften with heat and melt at a temperature proximate to the setting temperature. Low acyl gellan gum polymers typically have a range of the degree of acylation from about 1 to 2 glycerate per repeat and 1 to 2 acetate per every two repeats. The low acyl form of gellan gum generally requires a gelation agent such as salt or acid for gel formation. For example, low acyl gellan gum forms a firm, non-elastic, and brittle gel when cooled in the presence of gel-promoting cations, preferably divalent cations, such as calcium and magnesium.

In general, gellan gum as described above can dissolve in water at the temperature higher than 0° C. at a concentration of 0.001% to 10% w/v, while gellan gum of all types can dissolve completely in water at a temperature higher than 80° C. The gellan gum aqueous solution thus formed can maintain in a liquid form after dissolution or heating-cooling circle at temperature higher than 0° C. and pH of about 4-10.

The gellan gum as described above can be modified on the position of carboxyl moiety (i.e., red circled COO⁻ group in the figure below) with funcational peptide or moleculars through convealnt bond. Such modifications can be performed by heating the gellan gum and peptide/molecules mixing solution to 121° C. or higher temperature at high pressure (such as 15 psi) for a time of 3 minutes or longer. In addition, the aforementioned gellan gum solution can also be mixed with functional peptide or moleculars without convealnt binding.

The present invention provides a composition for preparing a polysaccharide hydrogel, wherein one or more chemical molecules modifying the gellan sum are selected from the group consisting of: a) organic molecules that are selected from the group consisting of: polymers of natural or synthetic origin, chemically modified or co-polymers, polypeptide, hyaluronate, chitosan, collagen, polyethyleneglycol anticoagulants, contrasting agents, chemotherapeutic agents, and signaling pathway molecules; and b) inorganic molecules that are selected from the group consisting of: bioactive glass, hydroxyapatite, calcium phosphate and iron.

According to one embodiment of the present invention, the water soluble low acyl gellan gum, high acyl gellan gum, modified gellan gum and a mixture of gellan gum mixture with other chemical/biological molecules, as described above, are suitable for such applications of gellan gum for cell culture and other biomedical application. The selected group of gellan gum can dissolve in water or maintain dissolved in liquid form at room temperature, perform a neutral pH (pH 4-10) and keep the liquid or semi-gel state when surrounding temperature is at or above refrigerator temperature. The gellan gum solution can have various concentrations of 0.001-10% solid contain or chemical modification (e.g. methacrylate) to achieve higher concentration.

The preparing method for gellan gum solution including dissolving gellan gum in water based solution with a solid content from about 0.001% w/v to 10% (w/v), heating the solution to a temperature ranging from about 100° C. to about 150° C. and preferably from about 100° C. to about 121° C. and under a pressure ranging from about 1 psi to about 40 psi, preferably a pressure ranging from about 1 psi to about 30 psi for a time period from about 3 to about 30 minutes, preferably from about 5 to about 20 minutes. Such preparation method also applied to preparing biological molecular modified gellan gum solution. Such biological molecules are selected from the group consisting of: cells, peptides, proteins, lipids, polysaccharides, growth factors, growth hormone, antibodies, enzymes, cell receptors, cell ligands, antibiotics, anti-microbial, anti-fungi, antimycotics, albumin, serum, functional peptide molecules with $NH_2$, COOH and $CONH_2$ group comprising: RGD, IKVAV, REDV, YIGSRY, poly Lysine. The water-based solvent used in such a preparation method comprises water, phosphate buffer solution (PBS), saline solution, cell culture medium, ionic solution, albumin, serum and xyloglucan The present invention provides a composition for preparing a polysaccharide hydrogel, wherein the composition comprises from about 0.001% to about 20% of the one or more high acyl gellan gum polymers, about 0.001% to about 20% of the one or more low acyl gellan gum polymers, about 0.001% to about 20% of the one or more modified gellan gum polymers, and further comprises from about 0.00001% to about 30% of the one or more bioactive molecules.

In a preferred embodiment, the composition comprises from about 0.01% to about 5% of the one or more high acyl gellan gum polymers, about 0.01% to about 5% of the one or more low acyl gellan gum polymers, about 0.01% to about 5% of the one or more modified gellan gum polymers, and further comprises from about 0.001% to about 10% of the one or more bioactive molecules.

The gellan gum solution can be trigger into hydrogel by directly mixing with water-based solvents, which include, but are not limited to, phosphate buffer (PBS), cell culture media or ionic solutions at a temperature ranging from about 4° C. to about 60° C. The storage modulus (G') of the system increases upon mixing and surpasses about 10 Pa within 30 min, and in a preferred embodiment, storage modulus (G') of the system surpasses about 10 to 20000 Pa, which indicate the system is stronger enough to suspend cells within its hydrogel matrix for 3D growth. The trigger solution using for this hydrogel formation can be any type of cell culture media with or without serum, buffers, ionic solutions with pure or mixture of mono, divalent or polyvalent cations or the mixture of above solutions.

Figure 2:
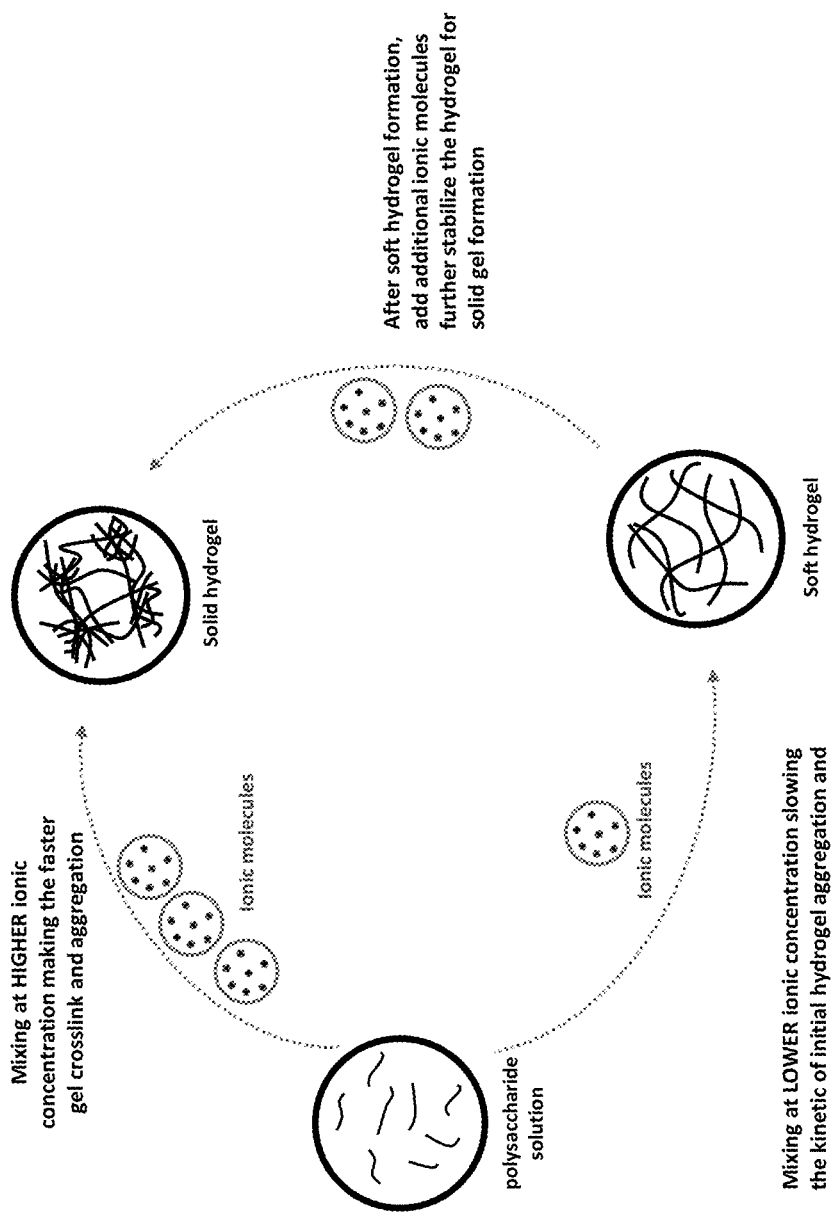
FIG. 2 is a diagram detailing formation of the soft and hard hydrogels of embodiments of the present invention.

Referring now to FIGS. 1 and 2, two type of hydrogel with different rheological properties can be formed depending on the mixing ratios and ionic concentrations of solutions forming the hydrogel. A soft hydrogel comprising a fiber structure can be formed when the gellan gum solution and trigger solution are mixed from 100:1 to 1:1 ratios. Preferably, the mixing ratio is 4:1 to 1:1. The soft hydrogel possesses a shear thinning and self-healing rheological property, which allow the hydrogel be converted into a liquid state by shearing force (such as pipetting, syringe injection or pump perfusion) but rapidly recover its hydrogel state once the external force is ceased. The gel-sol state can be transformed multiple times. Cells and biomolecules can be embedded within the hydrogel and deliver to a different location by injection. The mixing is typically performed at a temperature from about 4 to about 60° C., preferably at room temperature to about 37° C. Ion trigger solution contains one or more positive ionic molecular such as $Na+$, $K+$, $Ca++$, $Mg++$ etc. The ionic concentration higher than 0.01%.

Figure 3:
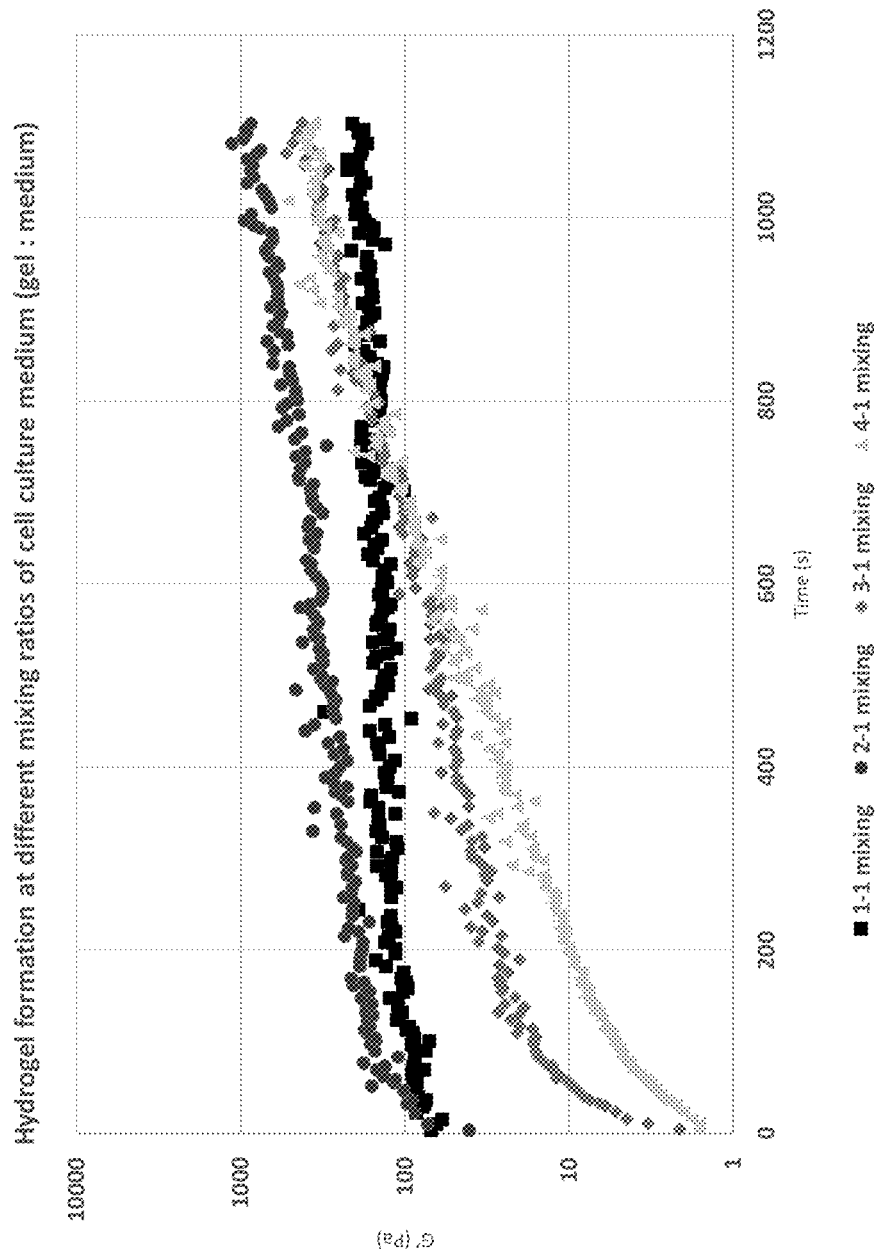
FIG. 3 is a graph illustrating the rheological data of the hydrogel formation at different mixing ratios.

A hard hydrogel comprising an agglomeration structure can be formed with the gellan gum solution and trigger solution are mixed from 1:1 to 1:100 ratios or when the trigger solution contain high ionic concentration. Preferably, as shown in FIG. 3, the mixing ratio is 1:1 to 1:4 and the trigger solution has an ion (e.g., $Ca2+$) concentration higher than 0.02% w/v. In a preferred embodiment, the mixing range for hydrogel formation is 4:1 v/v (4 parts of gellan gum solution mixed with 1 part of cell culture medium) to 1:4 (1 part of gellan gum solution mixed with 4 part of cell culture medium). The hard hydrogel is stiff and brittle and doesn't possess the shear thinning and self-healing rheological property. When disturbed with external force, the hard hydrogel can be broke into small gel particles. The hard hydrogel can maintain its hydrogel formation when it is placed in an 80° C. water bath. In the aforementioned preferred embodiment, the hard hydrogel formed can maintain its hydrogel formation at a temperature as high as 80° C.

Additionally, the soft gel can be converted to hard gel when an additional ionic solution is added into the hydrogel system, such as by covering with or submerging in extra phosphate buffer, cell culture media or ionic solutions. As an example: mixing 800 μL 1% gellan gum solution with 200 μL DMEM medium will form a soft gel. After soft gel is formed, adding 1 mL DMEM medium on the top of the soft gel will convert the soft hydrogel into hard hydrogel within 12 hours.

This transformation provides a convenient two-step procedure for in vitro 3D cell culture in this hydrogel system. Bioactive molecules can be directly mixed with cell culture medium before mixing with gellan gum solution added to the hydrogel afterward. Such biological molecules can be such as cells, peptides, proteins, lipids, polysaccharides, growth factors, growth hormone, antibodies, enzymes, cell receptors, serum, cell ligands, antibiotics, anti-microbial, anti-fungi, antimycotics.

Living cells can be mixed with gellan gum solution or trigger solution such as cell culture media before the hydrogel formation. The cells are homogeneously suspended in the soft hydrogel and ready to transfer to an individual good plate or different container by pipetting or injection. Once the soft gel (with cells) is placed in the final container, the extra trigger solutions can be added on the top or surround the soft gel and convert it into the hard hydrogel. This procedure not only further stabilized the 3D matrix structure but also allow nutrition or other biomolecules to be added into the hydrogel system and exchange between the hydrogel and surrounding media. The embedded cells can grow as 3D colonies and use for drug discovery, high-throughput screen or basic biological study. A similar procedure can be used to coat cell culture plate or devices: the soft gel is added directly to the surface of the culture plate and then living cells can be added on the top of hydrogel and grow in 2D. This type of application can be used for cell migration and invasion study, some cells can penetrate into hydrogel from the top and grow as 3D structure. Cells can be harvested out of hydrogel by breaking the hydrogel and dissolve the hydrogel with DI water or low ionic concentration solution.

Biomolecules such as a functional peptide, protein, growth factor, drug compound can be added into the hydrogel system before or after hydrogel formation and exchange of hydrogel and the surrounding media. This property makes this 3D cell culture hydrogel system suitable for cell viability assay, live/dead assay, fluorescent staining, and imaging and histological analysis. In addition, the bioactive compound can be also covalent binding to gellan gum molecules through chemical modification and increase interaction between hydrogel matrix and cells.

Overall, the hydrogel can be used for 3D cell culture, 2D coating, a carrier for different bioactive molecules for slow release, injection, bioprinting, etc.

EXAMPLES

Figure 4:
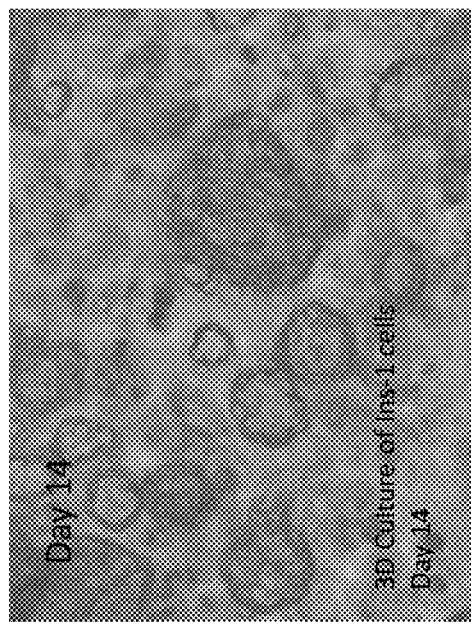
FIG. 4 illustrates images of a 3D cell culture of BetaTC3 cells and Ins-1 cells in a hydrogel of an embodiment of the present invention.
Figure 4:
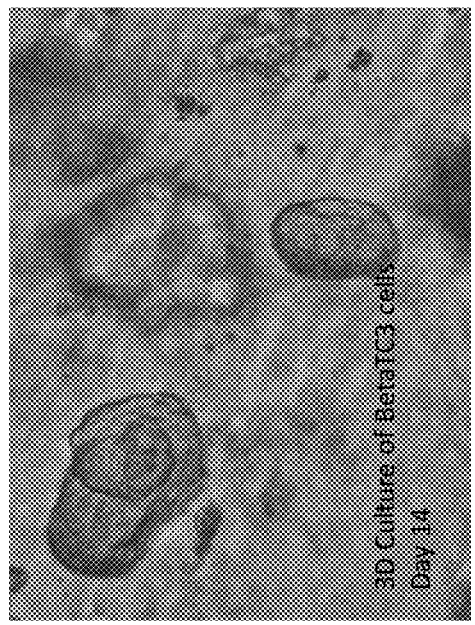
Figure 5:
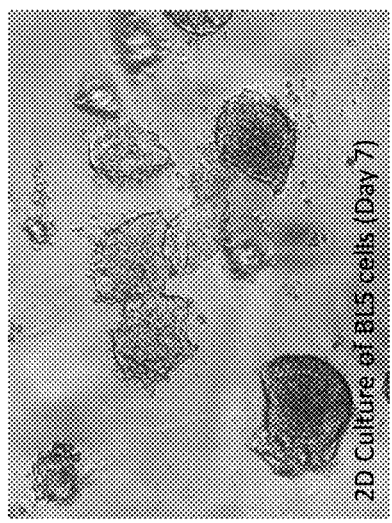
FIG. 5 illustrates images of a 2D cell culture of BL5 cells in a hydrogel of an embodiment of the present invention.

Example 1 (as Shown in FIG. 4): Prepare BetaTC3 Cells Suspension at $5 \times 10^5$ Cells/mL in DMEM Medium Prepare the gellan gum solution at 1% w/v. Mixing the gellan gum solution with cell suspension at 4:1 ratio (v/v). The gelation would start right after mixing, showing an increasing of G'. The soft hydrogel can be formed in 15 min by showing the G'>50 pa. The BetaTC3 cells suspended within the hydrogel. After that, adding a more DMEM medium on the top of the soft gel, the hydrogel would be further stabilized by showing the increasing G'. A hard gel would form after 2 hours (or overnight) showing the G' higher than 500 Pa. The BetaTC3 cells can grow in the hydrogel and form 3D colonies after 3 days.

Example 2 (as Shown in FIG. 4): Prepare Ins-1 Cells Suspension at $5 \times 10^5$ Cells/mL in RPMI Medium Prepare the gellan gum solution at 1% w/v. Mixing the gellan gum solution with cell suspension at 1:1 ratio (v/v). The gelation would start right after mixing, showing an increasing of G'. The soft hydrogel can be formed in 15 min by showing the G'>50 pa. The Ins-1 cells suspended within the hydrogel. After that, adding more RPMI medium on the top of the soft gel, the hydrogel would be further stabilized by showing the increasing G'. A hard gel would form after 2 hours (or overnight) showing the G' higher than 300 Pa. The Ins-1 cells can grow in the hydrogel and form 3D colonies after 3 days.

The many elements of the present invention make it unique in the field. The novelty is illustrated by the various options for nearly every aspect of the invention that allow it to be used in the proper exercise form by a variety of users, both in terms of body size and fitness level. Additionally, there is a wide range of exercises available to any user of the present invention, and users can perform exercises that use the upper and lower extremity muscle groups simultaneously.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A composition for a soft polysaccharide hydrogel capable of conversion to a hard polysaccharide hydrogel, the soft polysaccharide hydrogel comprising:
   one or more water soluble high acyl gellan gum polymers;
   one or more water soluble low acyl gellan gum polymers; and
   one or more water soluble chemically modified gellan gum polymers or one or more peptide modified gellan gum polymers, wherein the soft polysaccharide hydrogel exhibits a homogeneous matrix structure and the hard polysaccharide hydrogel exhibits an aggregated matrix network structure.

2. The composition according to claim 1, wherein the soft polysaccharide hydrogel is suitable for injection uses.

3. The composition according to claim 2, wherein the soft polysaccharide hydrogel exhibits shear thinning and self-healing rheological properties, by allowing the soft polysaccharide hydrogel to be converted into a liquid state by a shearing force, or to recover its hydrogel state once the shearing force is ceased.

4. The composition according to claim 3, wherein the shearing force is exerted by pipetting, syringe injection, or pump perfusion or a combination thereof.

5. The composition according to claim 1, wherein the hard polysaccharide hydrogel exhibits 3-D gel structures with rheological properties such that when the hard gel is broken by pipetting or shearing, the hard gel breaks into smaller gel particles, and has an affinity for one or more bioactive molecules.

6. The composition according to claim 1, wherein the hard polysaccharide hydrogel has a storage modulus value of greater than about 10 Pa.

7. The composition according to claim 1, wherein the hard polysaccharide hydrogel maintains its gel formation at a temperature equal to or below about 80° C., but is capable of being broken into smaller gel particles when disturbed with an external force.

8. The composition according to claim 1, wherein the one or more chemically modified gellan gum polymers are selected from the group consisting of:
   a) organic molecules selected from the group consisting of: polymers of natural or synthetic origin, chemically modified or co-polymers, hyaluronate, chitosan, collagen, polyethyleneglycol anticoagulants, contrasting agents, chemotherapeutic agents, and signaling pathway molecules; and
   b) inorganic molecules selected from the group consisting of: bioactive glass, hydroxyapatite, calcium phosphate and iron.

9. The composition according to claim 5, wherein the one or more bioactive molecules are added into the gellan gum solution before heating are selected from the group consisting of: cells, peptides, proteins, lipids, polysaccharides, growth factors, growth hormone, antibodies, enzymes, cell receptors, cell ligands, antibiotics, anti-microbial, anti-fungi, antimycotics, and functional peptide molecules with an $NH_2$, a COOH and an $CONH_2$ group comprising: a tripeptide Arg-Gly-Asp (RGD) motif, a Ile-Lys-Val-Ala-Val (IKVAV) peptide, an Arg-Glu-Asp-Val (REDV) peptide, a laminin sequence Tyr-Ile-Gly-Ser-Arg (YIGSR), and poly-Lysine.

10. The composition according to claim 1, wherein the soft polysaccharide hydrogel is converted into the hard polysaccharide hydrogel by submerging the soft polysaccharide hydrogel in an aqueous solution of extra phosphate buffer, cell culture media, or ionic solutions, or a combination thereof.

11. The composition according to claim 1, wherein one or more bioactive molecules are in contact with, adhered to, or embedded in the soft and hard polysaccharide hydrogels while maintaining their bioactivities.

12. The composition according to claim 1, wherein each of the one or more bioactive molecules are suspended in or entrapped in the soft and hard polysaccharide hydrogels while maintaining their bioactivities.

13. The composition according to claim 1, wherein a solution of gellan gum modified by peptides is formed by adding peptide into the gellan gum solution as a mixture and then heating at a temperature of about 100° C. or above and a pressure of about 1 to about 40 psi, and for a time period of about 3 to about 30 min.

14. The composition according to claim 1, wherein the composition comprises from about 0.001% to about 20% of the one or more high acyl gellan gum polymers, about 0.001% to about 20% of the one or more low acyl gellan gum polymers, about 0.001% to about 20% of the one or more modified gellan gum polymers, and further comprises from about 0.00001% to about 30% of the one or more bioactive molecules.

15. The composition of according to claim 14, wherein the composition has a storage modulus value of about 10 Pa.

16. The composition according to claim 1, wherein the composition comprises from about 0.01% to about 10% of the one or more high acyl gellan gum polymers, about 0.01% to about 10% of the one or more low acyl gellan gum polymers, about 0.01% to about 10% of the one or more modified gellan gum polymers, and further comprises from about 0.001% to about 20% of the one or more bioactive molecules.

17. The composition of according to claim 16, wherein the composition has a storage modulus value of about 10 Pa to about 20000 Pa.

18. A method for forming a polysaccharide hydrogel according to claim 1, the method comprising the steps of:
   dissolving water-soluble gellan gum polymers in a water based solvent with a solid content higher than 0.001% w/v at a temperature ranging from about 4° C. to about 99° C.;
   heating the solution to a temperature of about 100° C. or higher and at a pressure of about 1 psi or higher for 3 minutes or longer; and reticulation at a temperature ranging from about 4° C. to about 60° C. by directly mixing the solution with phosphate buffer (PBS), cell culture media or ionic solutions to trigger the polysaccharide hydrogel formation, wherein a storage modulus (G') of the polysaccharide hydrogel increases upon mixing and surpasses about 10 Pa within 30 minutes such that the system sustains bioactive molecules suspended within its hydrogel matrix for 3D growth; and adding chemicals or bioactive molecules such that the chemicals or bioactive molecules are in contact with, adhered to, suspended, embedded or entrapped in the polysaccharide hydrogel formed.

19. The method according to claim 18, wherein the water based solvent comprises water, phosphate buffer solution (PBS), saline solution, and cell culture medium.

20. The method according to claim 18, the solid content is used in amounts ranging from about 0.001% (w/v) to 10% (w/v).

21. The method according to claim 18, wherein a soft hydrogel is formed when the solution and a trigger solution of an ionic concentration of about 0.01% (w/v) or higher are mixed with a ratio range from about 100:1 to about 1:1.

22. The method according to claim 18, wherein a hard hydrogel is formed when the solution and a trigger solution of a high ionic concentration of about 0.01% (w/v) are mixed with a ratio range from about 1:1 to about 1:100.

23. The method according to claim 18, wherein, a hard hydrogel is formed when the solution and a trigger solution of a normal ionic concentration of about 0.01% (w/v) are mixed with a ratio range from about 1:1 to about 1:20.

24. The method according to claim 18, wherein the solution is heated to a temperature ranging from about 100° C. to about 132° C. and preferably from about 100° C. to about 121° C. before reticulation.

25. The method according to claim 18, wherein the solution is heated under a pressure ranging from about 1 psi to about 25 psi before reticulation.

26. The method according to claim 18, wherein the solution is heated under a pressure ranging from about 1 psi to about 15 psi before reticulation.

27. The method according to claim 18, wherein the solution is heated for from about 1 minute to about 30 minutes before reticulation.

28. The method according to claim 18, wherein the solution is heated for from about 5 minutes to about 20 minutes before reticulation.

29. The composition according to claim 10, wherein the soft polysaccharide hydrogel formed is converted into the hard polysaccharide hydrogel by submersion in an aqueous solution of cell culture media or ionic solution.

30. The hard polysaccharide hydrogel formed and inter-converted by the method according to claim 10, wherein one or more bioactive molecules can be added to the hard polysaccharide hydrogel before or after the hard polysaccharide hydrogel formation, or before or after the exchange of hydrogel and the surrounding media, by being mixed with the gellan gum solution or trigger solutions.

31. A method of of a polysaccharide hydrogel, which is derived from a composition according to claim 1, as a versatile platform for drug discovery and biomedical applications, comprising cell viability assay, live/dead assay, high-throughput screening, fluorescent staining and imaging, histological analysis, and 3D bio-printing.

32. The method according to claim 31, wherein living cells are grown on the top of, or embedded, encapsulated in the hydrogel and are harvested out of hydrogel system by breaking the hydrogel and dissolving the hydrogel with DI water or low ionic concentration solution.

33. The method according to claim 31, wherein a two-step procedure is provided for in vitro 3D cell culture in the hydrogel, comprising:
1) living cells being mixed with gellan gum solution or trigger solution such as cell culture media before the hydrogel formation, wherein the cells are homogeneously suspended in the soft hydrogel and ready to transfer to an individual cell culture plate or different container by pipetting or injection; and
2) once the soft gel is placed in the final container, where the extra trigger solutions are added on the top or surround the soft gel and convert it into the hard hydrogel, wherein the 3D matrix structure is further stabilized and nutrition or other biomolecules are added into the hydrogel system and exchange between the hydrogel and surrounding media.

34. The method according to claim 31 for 2D hydrogel coating cell culture study, wherein the soft hydrogel is added directly to the surface of the culture plate to coat the cell culture plate, and then living cells can be added on the top of hydrogel and grow in 2D and some cells can penetrate into hydrogel from the top and grow as 3D structure.

35. The method of claim 18 further comprising the step of: adding sodium citrate to the water-soluble gellan gum polymers forming a gellan gum polymer solution; and adjusting the pH of the gellan gum polymer solution to a neutral pH.

36. The method of claim 21 wherein the soft hydrogel comprises a fiber structure suitable for injection.

37. The method of claim 22 wherein the hard hydrogel comprises an agglomeration structure.

38. The composition according to claim 12, wherein each of the one or more biomolecules are attached to, suspended in or entrapped in the aggregated matrix network structure of the hard polysaccharide hydrogel.

39. The composition according to claim 12, wherein each of the one or more biomolecules are attached to, suspended in or entrapped in the homogeneous matrix structure of the soft polysaccharide hydrogel.

40. The composition according to claim 1, wherein cells are added to a surface or suspended in or entrapped in the soft or hard polysaccharide hydrogel.

* * * * *